(12) United States Patent
Kumar et al.

(10) Patent No.: US 7,566,782 B2
(45) Date of Patent: Jul. 28, 2009

(54) PROCESS FOR THE PREPARATION OF ROSUVASTATIN

(75) Inventors: Yatendra Kumar, Haryana (IN); Hashim Nizar Poovanathil Nagoor Meeran, Kerela (IN); Shantanu De, New Delhi (IN); Mohammad Rafeeq, Uttar Pradesh (IN); Swargam Sathyanarayana, Andhra Pradesh (IN)

(73) Assignee: Ranbaxy Laboratories Limited, Gurgaon (IN)

( * ) Notice: Subject to any disclaimer, the term of this patent is extended or adjusted under 35 U.S.C. 154(b) by 488 days.

(21) Appl. No.: 10/537,859

(22) PCT Filed: Dec. 10, 2002

(86) PCT No.: PCT/IB02/05213

§ 371 (c)(1),
(2), (4) Date: Nov. 9, 2005

(87) PCT Pub. No.: WO2004/052867

PCT Pub. Date: Jun. 24, 2004

(65) Prior Publication Data

US 2006/0149065 A1    Jul. 6, 2006

(51) Int. Cl.
| C07D 239/42 | (2006.01) |
| C07D 403/12 | (2006.01) |
| C07D 413/12 | (2006.01) |
| C07F 9/535 | (2006.01) |
| C07F 7/18 | (2006.01) |
| A61K 31/505 | (2006.01) |
| A61K 31/506 | (2006.01) |
| A61P 3/06 | (2006.01) |
| A61P 3/10 | (2006.01) |

(52) U.S. Cl. .................. 544/332; 556/437; 560/175
(58) Field of Classification Search ............... 544/332
See application file for complete search history.

(56) References Cited

U.S. PATENT DOCUMENTS 5,260,440 A    11/1993    Hirai et al. ............... 544/322

FOREIGN PATENT DOCUMENTS

EP    0 521 471    1/1993

*Primary Examiner*—Venkataraman Balasubramanian
(74) *Attorney, Agent, or Firm*—George E. Heibel, Esq.

(57) ABSTRACT

The present invention relates to a process for the preparation of rosuvastatin calcium, a promising new HMG-CoA reductase inhibitor.

17 Claims, No Drawings

PROCESS FOR THE PREPARATION OF ROSUVASTATIN

FIELD OF THE INVENTION

The present invention relates to a process for the preparation rosuvastatin, a promising new HMG-CoA reductase inhibitor.

BACKGROUND OF THE INVENTION

HMG-CoA reductase inhibitors, popularly known as statins, are among the most widely prescribed lipid—lowering drugs.

Chemically rosuvastatin is (+)-(3R,5S)-7-[4-(4-Fluorophenyl)-6-isopropyl-2-(N-methyl-N-methanesulfonylamino) pyrimidin-5-yl]3,5-dihydroxy-6(E)-heptenoic acid calcium salt (2:1) having the structural formula I.

FORMULA I

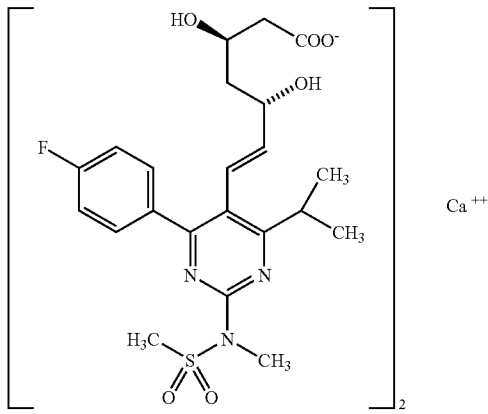

Rosuvastatin is an antihypercholesterolemic drug used in the treatment of atherosclerosis.

Hypercholesterolemia is now well recognized as a primary risk in coronary heart disease. Clinical studies with lipid lowering agents have established that decreasing elevated serum cholesterol level reduces the incidence of cardiovascular mortality. Recently, it has been found that rosuvastatin calcium has consistently shown greater potency than other currently marketed statins (atorvastatin, simvastatin and pravastatin) in preclinical and clinical testing.

Rosuvastatin and a process for its preparation is disclosed in U.S. Pat. No. 5,260,440. The process disclosed therein involves four distinct chemical steps: (1) condensation of methyl (3R)-3-[(tert-butyldimethylsilyl) oxy]-5-oxo-6-triphenylphosphoranyli-dene hexanoate with 4-(4-fluorophenyl)-6-isopropyl-2-(N-methyl-N-methanesulfonylamino)-5-pyrimidinecarboxaldehyde; (2) deprotection of the 3-hydroxyl group to give the keto alcohol; (3) reduction of 5-oxo to get the chiral dihydroxy heptenoate; and (4) hydrolysis of the dihydroxy heptenoate.

The generation of the phosphorane side chain requires eight synthetic steps and involves expensive reagents. The process is both uneconomical and time consuming, hence not suitable for commercial production.

It is, therefore, desirable to provide an efficient process for the preparation of rosuvastatin which improves the economics by employing less expensive reagents and is more productive.

SUMMARY OF THE INVENTION

The present invention provides a process and novel intermediates for the preparation of rosuvastatin, its salts, esters, or the corresponding cyclized lactone form. The process provides obvious benefits with respect to economics and convenience to operate on a commercial scale.

DETAILED DESCRIPTION OF THE INVENTION

The present invention provides a process for the preparation of rosuvastatin of structural formula I as shown in Scheme I or the corresponding ring closed lactone form, comprising:

(a) condensing 1-cyano(2S)-2-[(tert-butyldimethylsilyl) oxy]4-oxo-5-triphenylphos-phororanylidene pentane of structural formula II with 4-(4-Fluorophenyl)-6-isopropyl-2-(N-methyl-N-methanesulfonylamino)-5-pyrimidinecarbaldehyde of structural formula III to give a condensed product of structural formula IV, (b) deprotecting the tert-butyldimethylsilyl group of the condensed product to afford a cyanoketo alcohol of structural formula V, (c) reducing the cyanoketo alcohol to cyanodiol of structural formula VI, and (d) hydrolyzing the cyanodiol of structural formula VI to produce said compound of structural formula I in free acid form, or in the form of an ester or a lactone thereof, or in salt form.

Scheme I

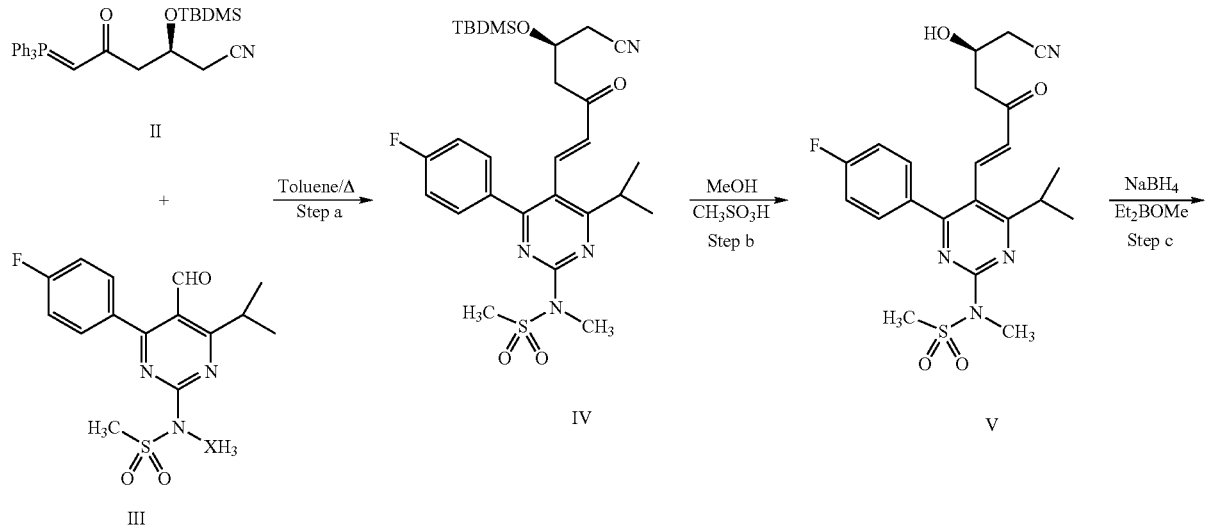

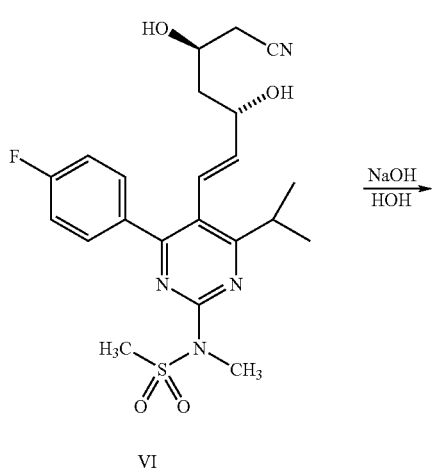 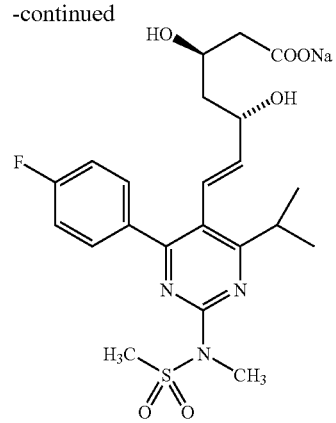 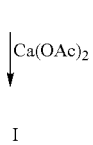 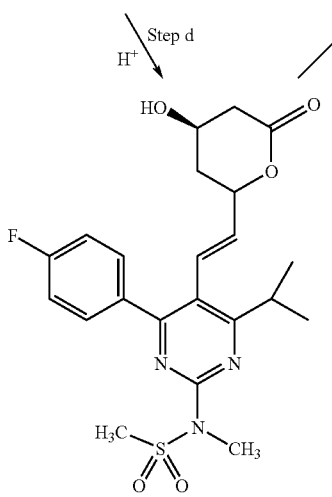

The condensation at step (a) is performed in the presence of an organic solvent, especially such as toluene, benzene, cyclohexane, heptanes, acetonitrile, tetrahydrofuran, dioxane and ethyl acetate. The reaction is carried out for about 1 to about 100 hours.

The deprotection of the tert-butyldimethylsilyl group at step (b) is performed in an organic solvent in the presence of acids or tetrabutylammonium fluoride to give a cyanoketo alcohol of formula V.

The organic solvent is selected from solvents such as sulfolane, dioxane, dimethylsulfoxide, dimethylacetamide, N-methyl pyrrolidone, acetonitrile, diethyl ether, tetrahydrofuran, dimethylformamide, and lower alcohols such as methanol, ethanol, propanol.

The acids used for deprotection are selected from sulfonic acids such as methanesulfonic acid, trifluoromethane sulfonic acid, inorganic acids such as hydrochloric acid, sulfuric acid nitric acid, phosphoric acid and organic acids such as formic acid, trifluro acetic acid, acetic acid.

The cyanoketo alcohol of formula V obtained in step (b) is reduced with diethylmethoxyborane and sodium borohydride. The reduction is performed in an organic solvent mixture comprising alcohols and non-alcoholic sovents. The reaction is worked up after completion to afford cyanodiol of formula VI.

The organic solvent mixture includes alcohols such as methanol, ethanol, propanol and butanol. The non-alcoholic organic solvent includes solvents such as acetonitrile, diethyl ether, tetrahydrofuran and dimethylformamide.

The reaction at step (c) is performed at a temperature from about $-100°$ C. to about $20°$ C., for example from about $-80°$ C. to about $-70°$ C. under cooling for about 10 minutes to about 20 hours, for example for about 30 minutes to about 10 hours.

The cyanodiol of formula VI is hydrolyzed by acids at step (d) to afford lactone of formula VII. Acids, which may be used, include inorganic acids such as hydrochloric acid, sulfuric acid and the like. The cyanodiol of Formula VI can be directly converted to its sodium salt of formula VIII.

The lactone obtained in step (d) is converted into its sodium salt of formula VIII and then to its hemicalcium salt of rosuvastatin of formula I by treatment with calcium acetate.

In another aspect of the invention, rosuvastatin is prepared by a process which comprises treatment of the condensed product of structural formula IV with an alcohol, such as methanol, ethanol, propanol, and the like and an acid such as hydrochloric acid to provide an ester of formula IX

FORMULA IX

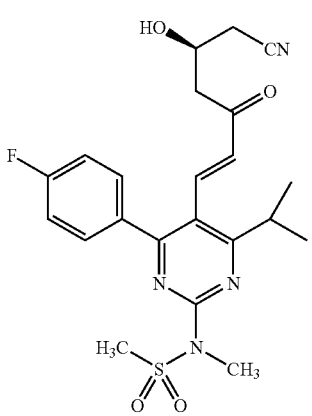

which is reduced to provide a compound of formula X,

FORMULA X

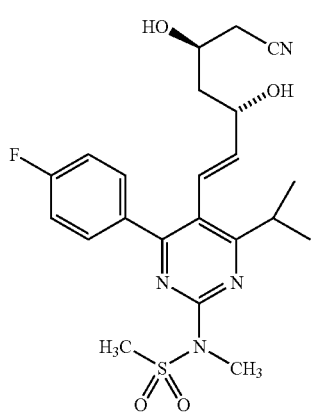

which in turn, is hydrolyzed to give rosuvastatin by the same method as described in steps (c) and (d) of Scheme I.

The starting material of formula III may be prepared, for example, as described in U.S. Pat. No. 5,260,440.

The methods known in the art may be used with the process of this invention to enhance any aspect of the process. The product obtained may be further purified by any technique known to a person skilled in the art, for example, crystallization, column chromatography, preparative high pressure liquid chromatography, preparative thin layer chromatography, extractive washing in solution or a combination of these procedures.

In the following examples, the preferred embodiments of the present invention are described only by way of illustrating the process of the invention. However, these are not intended to limit the scope of the present invention in any way.

EXAMPLES

Preparation of rosuvastatin (+)-(3R,5S)-7-[4-(4-fluorophenyl)-6-isopropyl-2-(N-methyl-N-methanesulfonylamino) pyrimidin-5-yl]-3,5-dihydroxy-6(E)-heptenoic acid calcium salt (2:1).

Example 1

Step A

Preparation of Condensed Product N-[5-[-(tert-Butyl-dimethyl-silanyloxy)-6-cyano-3-oxo-hex-1-enyl]-4-(4-fluorophenyl)-6-isopropyl-pyrimidin-2-yl]-N-methyl-methanesulfonamide (Condensed Product, Formula IV)

To a solution of pyrimidine aldehyde (1.0 gm) of Formula III in toluene (20 ml), 1-cyano (2S)-2-[(tert-butyldimethylsilyl)oxy]-5-oxo-6-triphenylphosphanylidene hexanenitrile of formula II was added and the reaction mixture was refluxed for about 24 hours. The reaction mixture was concentrated and the residue titurated with cyclohexane (50 ml). The cyclohexane layer was concentrated to give a residue which was purified by silica gel chromatography, eluted with toluene to obtain 1.60 gm of the condensed product as a thick oil.

Step B

Preparation of cyanoketo alcohol-N-[5-(6-cyano-5-hydroxy-3-oxo-hex-1-enyl)4-(4-fluoro-phenyl)-6-isopropyl-pyrimidin-2-yl]-N-methyl-methanesulfonamide (Cyanoketo Alcohol, Formula V)

To a solution of the condensed product (1.0 gm) in methanol (10 ml), a solution of (0.8 ml) of methanesulfonic acid in water (4.6% w/w) was added dropwise at 10-15° C. The reaction mixture was stirred for 24 hours at room temperature, concentrated and the residue was dissolved in methylene chloride (10 ml). The solution was washed with 1% sodium bicarbonate followed by brine. The organic layer was concentrated to give a residue which was purified by column chromatography over silica gel, eluted with toluene to give (0.65 gm) cyanoketo alcohol as a solid.

Step C

Preparation of cyanodiol N-[5-(6-cyano-3,5-dihydroxy-hex-1-enyl)-4-(4-fluoro-phenyl)-6-isopropyl-pyrimidin-2-yl]-N-methyl-methanesulfonamide. (Cyanodiol, Formula VI)

To a solution of the cyanoketo alcohol (1.0 g) in tetrahydrofuran (THF)(25 ml), methanol (7 ml) was added and the solution was cooled to −78° C. Diethylmethoxy borane (2.3 ml) in THF (1M) at −76° C. to −78° C. was added to the reaction mixture. The reaction mixture was stirred for 30 min and sodium borohydride (0.10 gm) was added. The reaction mixture was further stirred at the same temperature for 3 hours and the temperature was allowed to rise to 25° C. in 45 minutes. Acetic acid (1.4 ml) was added and stirred for 10 min. The solvent was evaporated under vacuum and then methanol (10 ml) was added which was also evaporated off. Ethyl acetate (10 ml) was added and the solution was washed with aqueous sodium bicarbonate solution (3 ml). The organic layer was washed with brine (5 ml) and then dried over sodium sulfate. The concentration of the solution under reduced pressure yielded cyanodiol as oil (0.8 gm).

Step D

Preparation of Rosuvastatin

Conc. HCl (2.5 ml) was added to the cyanodiol (0.5 gm) and the reaction mixture was stirred at room temperature for 12 hours. The resulting solution was diluted with water (2.5 ml), cooled to 50° C. and then neutralized with 1% aqueous sodium bicarbonate. The resulting mixture was extracted with ethyl acetate (10 ml). The ethyl acetate layer was concentrated and the resulting residue was dissolved in toluene (10 ml). The toluene solution was refluxed for 2 hours and the solvent was evaporated to give rosuvastatin lactone. Ethanol (7 ml) was added to the residue and stirred for 60 min followed by the addition of 0.1 N aqueous NaOH (11 ml). Ethanol was evaporated under vacuum, followed by the dropwise addition of a solution of calcium acetate. After stirring for 2 hours, the product was filtered, washed and dried to give rosuvastatin hemicalcium salt (0.26 g).

Example 2

Preparation of Rosuvastatin from Methyl Ester of Formula IX

HCl gas was bubbled into a suspension of the condensed product (1.0 gm) of formula IV in methanol (10 ml) at −40° C. to −20° C. for 2.5 hours. The resulting solution was stirred at 0° C. for 15 hours and then the solvent was removed. The residue was taken in ethyl acetate and washed with water (10 ml). The pH of the organic layer was adjusted to 4.5 with aqueous sodium bicarbonate. The ethyl acetate layer was separated, washed with water and then with brine. The organic layer was concentrated to give a residue which was purified by column chromatography over silica gel to give 0.8 gm methyl ester of formula IX.

The methyl ester obtained above was reduced in the same way as described in step (c) of Example 1. Subsequent hydrolysis to the acid, its sodium salt formation and further conversion to the calcium salt was prepared as described in step (d) of Example 1 which afforded rosuvastatin hemicalcium salt (0.5 g).

While the present invention has been described in terms of its specific embodiments, certain modifications and equivalents will be apparent to those skilled in the art and are intended to be included within the scope of the present invention.

What is claimed is:

1. A process for producing rosuvastatin of structural formula I,

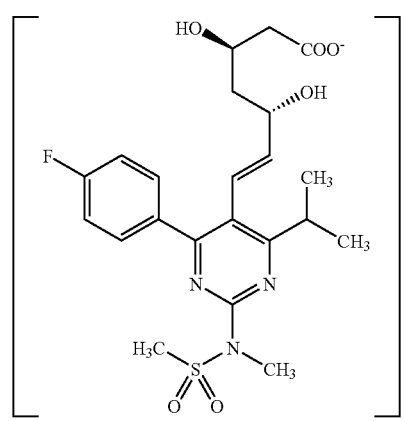

FORMULA I comprising:
a. condensing 1-cyano (2S)-2-[(tert-butyldimethylsilyl)oxy]-5-oxo-6-triphenylphosphanylidene hexanenitrile of structural formula II

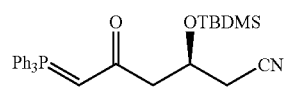

FORMULA II with 4-(4-Fluorophenyl)-6-isopropyl-2-(N-methyl-N-methanesulfonylamino)-5-pyrimidinecarbaldehyde of structural formula III

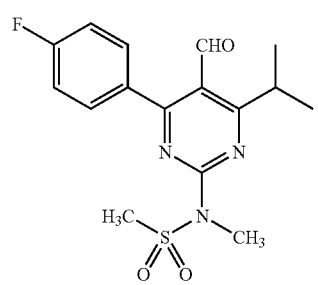

FORMULA III to give a condensed product of structural formula IV

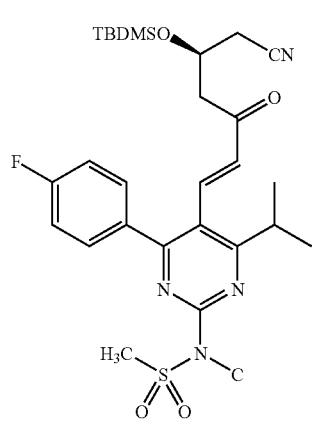

FORMULA IV b. deprotecting of the tert-butyldimethylsilyl group of the condensed product to afford a cyanoketo alcohol of structural formula V,

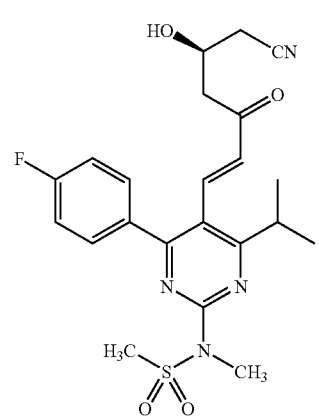

FORMULA V c. reducing the cyanoketo alcohol to cyanodiol of structural formula VI,

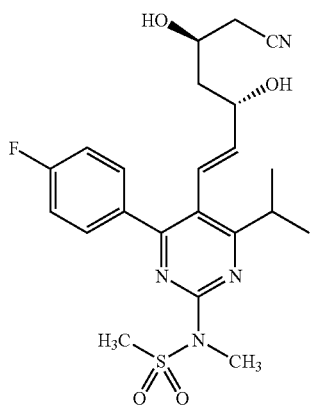

FORMULA VI d. hydrolyzing the cyanodiol of structural formula VI.

2. The process of claim 1 wherein step (a) is carried out in an organic solvent.

3. The process of claim 2 wherein the organic solvent is selected form the group consisting of toluene, benzene, cyclohexanes, heptanes and mixture(s) thereof.

4. The process of claim 3 wherein the organic solvent is toluene.

5. The process of claim 1 wherein step (b) is performed in an organic solvent.

6. The process of claim 5 wherein the organic solvent is selected from the group consisting of sulfolane, dioxane, dimethyl sulfoxide, dimethyl acetamide, N-methyl pyrrolidone, acetonitrile, diethyl ether, tetrahydrofuran, dimethylformamide, methanol, ethanol, propanol, and mixtures thereof.

7. The process of the claim 6 wherein the organic solvent is methanol.

8. The process of clam 1 wherein the deprotection at step (b) is performed by treating with acids or tetrabutylammonium fluoride.

9. The process of claim 8 wherein the acid is selected from the group consisting of methanesulfonic acid, trifluoromethanesulfonic acid, hydrochloric acid, sulfuric acid, nitric acid, phosphoric acid, formic acid, trifluoroacetic acid, and acetic acid.

10. The process of claim 9 wherein the acid is methanesulfonic acid.

11. The process of claim 1 wherein the reduction at step c is carried out in the presence of diethylmethoxyborane and sodium borohydride.

12. The process of claim 11 wherein the reduction is performed in an organic solvent mixture comprising an alcohol and a non-alcoholic solvents.

13. The process of claim 12 wherein the alcohol is selected from the group consisting of methanol, ethanol, propanol and butanol.

14. The process of claim 13 wherein the alcohol is methanol.

15. The process of claim 12 wherein the non-alcoholic organic solvent is selected from the group consisting of acetonitrile, diethyl ether, tetrahydrofuran and dimethylformamide.

16. The process of claim 15 wherein the non-alcoholic organic solvent is tetrahydrofuran.

17. The process of claim 1 wherein the hydrolysis at step (d) is performed after the reaction at step c is completed.

* * * * *